United States Patent [19]  
Nakao et al.

[11] Patent Number: 4,931,443  
[45] Date of Patent: Jun. 5, 1990

[54] PIPERAZINE COMPOUND AND PHARMACEUTICAL USE THEREOF

[75] Inventors: Toru Nakao, Nakatsu; Kenji Morita, Kiyose; Minoru Obata; Yasuto Morimoto, both of Nakatsu, all of Japan

[73] Assignee: Yoshitomi Pharmaceutical Industries, Ltd., Osaka, Japan

[21] Appl. No.: 219,543

[22] PCT Filed: Oct. 22, 1987

[86] PCT No.: PCT/JP87/00817  
§ 371 Date: Jun. 24, 1988  
§ 102(e) Date: Jun. 24, 1988

[87] PCT Pub. No.: WO88/03136  
PCT Pub. Date: May 5, 1988

[30] Foreign Application Priority Data

Oct. 27, 1986 [JP] Japan ................. 61-256446

[51] Int. Cl.$^5$ ............... A61K 31/495; C07D 403/10; C07D 403/14
[52] U.S. Cl. ............... 514/252; 514/235.8; 544/121; 544/295; 544/372; 544/374; 544/394
[58] Field of Search ............... 544/372, 374; 514/252
[56] References Cited

U.S. PATENT DOCUMENTS 3,941,789  3/1976  Renth et al. .................. 544/372
3,956,314  5/1976  Strubbe et al. ................. 548/558
4,219,551  8/1980  Seidelmann et al. ............ 544/372

OTHER PUBLICATIONS

Witte et al., Chemical Abstracts, vol. 99, No. 105277t (1983).
Goldstein et al., *Journal of Pharmacology and Experimental Therapeutics*, 249, p. 673 (1989).

Primary Examiner—Anton H. Sutto  
Assistant Examiner—E. Bernhardt  
Attorney, Agent, or Firm—Wenderoth, Lind & Ponack

[57] ABSTRACT

A piperazine compound represented by the general formula:

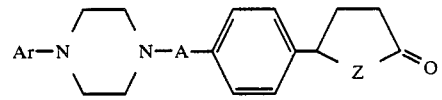

(wherein each of the symbols is as defined above) or a pharmaceutically acceptable acid addition salt thereof, and pharmaceutical uses thereof as well as intermediates thereof are disclosed. The above piperazine compounds possess antipsychotic activities with less adverse reaction on the extrapyramidal system and are useful as drugs.

3 Claims, No Drawings

PIPERAZINE COMPOUND AND PHARMACEUTICAL USE THEREOF

FIELD OF THE INVENTION

The present invention relates to a new and therapeutically useful piperazine compound or a pharmaceutically acceptable salt thereof, and to its pharmaceutical use as well as to an intermediate for its synthesis.

BACKGROUND OF THE INVENTION

Until now, a wide variety of antipsychotic drugs have been developed for the treatment of schizophrenia, mania, etc. Most of these drugs, however, are often found to cause extrapyramidal symptoms which are represented by delayed dyskinesia, Parkinson's disease, etc. in patients receiving continuous administration over a long period and make it difficult for the patients to participate in a social life or return to society.

DISCLOSURE OF THE INVENTION

Taking note of this fact, the present inventors made studies to develop an antipsychotic drug with less adverse reaction on the extrapyramidal system, thus completing the present invention. Accordingly, the present invention relates to a piperazine compound represented by the general formula:

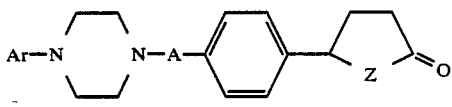 (I)

wherein Ar represents aryl or heteroaryl; A represents lower alkylene; Z represents —O— or —NR— [wherein R represents a hydrogen atom, lower alkyl, aryl, aralkyl, acyl, a group represented by the formula:

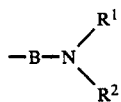 (a)

(wherein $R^1$ and $R^2$ independently represent a hydrogen atom, lower alkyl, aralkyl or a group which cooperates with the adjacent nitrogen atom to form a 5 to 7-membered heterocycle; B represents lower alkylene) or a group represented by the formula:

—CONHR³ (b)

(wherein $R^3$ represents a hydrogen atom, lower alkyl, lower alkenyl or aryl)], or a pharmaceutically acceptable acid addition salt thereof.

In the present specification, lower alkyl means straight-chain or branched-chain alkyl with 1 to 4 carbon atoms, including methyl, ethyl, propyl, isopropyl, butyl, isobutyl and tert-butyl; lower alkenyl means straight-chain or branched-chain alkenyl with 1 to 4 carbon atoms, including vinyl, 1-propenyl, allyl, isopropenyl and 2-butenyl; aryl includes phenyl and naphthyl or phenyl and naphthyl bearing on their aromatic ring at least 1 substituent chosen from halogen (chlorine, bromine, iodine and fluorine), lower alkyl, lower alkoxy (straight-chain or branched-chain alkoxy with 1 to 4 carbon atoms, e.g. methoxy, ethoxy, propoxy, isopropoxy, butoxy, isobutoxy and tert-butoxy), hydroxyl group, trifluoromethyl, cyano, nitro and amino; aralkyl includes benzyl, phenylethyl, phenylpropyl, phenylbutyl, naphthylmethyl, naphthylethyl, naphthylpropyl and naphthylbutyl or benzyl, phenylethyl, phenylpropyl, phenylbutyl, naphthylmethyl, naphthylethyl, naphthylpropyl and naphthylbutyl bearing on their aromatic ring at least 1 substituent chosen from halogen, lower alkyl, lower alkoxy, hydroxyl group, trifluoromethyl, cyano, nitro and amino; heteroaryl includes pyridyl, pyrimidyl, thienyl and furyl or pyridyl, pyrimidyl, thienyl and furyl bearing on their ring at least 1 substituent chosen from halogen, lower alkyl, lower alkoxy, hydroxyl group, trifluoromethyl, cyano, nitro and amino; the 5 to 7-membered heterocycle formed with a nitrogen atom may further have oxygen, sulfur or —NR⁴— (wherein $R^4$ represents hydrogen, lower alkyl, hydroxy lower alkyl, aryl or aralkyl) as heteroatoms, including pyrrolidinyl, piperidino, piperazinyl, 4-methyl-1-piperazinyl, 4-(2-hydroxyphenyl)-1-piperazinyl, 4-phenyl-1-piperazinyl, 4-benzyl-1-piperazinyl, morpholino, thio-morpholino and homopiperidino; acyl includes acetyl, propionyl, butyryl, pivaloyl, benzoyl, phenylacetyl, phenylpropionyl and phenylbutyryl or benzoyl, phenylacetyl, phenylpropionyl and phenylbutyryl bearing on their phenyl nucleus at least 1 substituent chosen from halogen, lower alkyl and lower alkoxy; lower alkylene means straight-chain or branched-chain alkylene with 1 to 4 carbon atoms, including methylene, ethylene, trimethylene, propylene, tetramethylene, 1-methyltrimethylene and 2-methylmethylene.

Examples of pharmaceutically acceptable acid addition salts of the compound (I) of the present invention include inorganic acid salts such as hydrochloride, hydrobromide, sulfate and phosphate, and organic acid salts such as maleate, fumarate, citrate, methanesulfonate, tartarate and pamoate.

The compounds of the general formula (I) which are preferable for the present invention among compounds defined above are the compounds which specifically have phenyl or phenyl having 1 to 2 substituents chosen from halogen, lower alkyl, lower alkoxy and trifluoromethyl for Ar, lower alkylene for A and —NR— for Z.

The more preferable compounds include 5-[4-(4-(4-(3-trifluoromethylphenyl)piperazin-1-yl)butyl)phenyl]-pyrrolidin-2-one, 5-[4-(4-(2-(4-(3-trifluoromethylphenyl)piperazin-1-yl)ethyl)phenyl]pyrrolidin-2-one, 5-[4-(4-(4-(3-methylphenyl)piperazin-1-yl)propyl)-phenyl]pyrrolidin-2-one, 5-[4-(3-(4-phenyl-piperazin-1-yl)propyl)phenyl]pyrrolidin-2-one, 5-[4-(4-(4-(4-fluorophenyl)piperazin-1-yl)butyl)phenyl]pyrrolidin-2-one, 5-[4-(4-(4-(2-methoxy-phenyl)piperazin-1-yl)butyl)phenyl]pyrrolidin-2-one and pharmaceutically acceptable acid addition salts thereof.

The compounds of the general formula (I) of the present invention can be produced by the methods described below.

(1) Compounds having —O— or —NH— for Z can be produced by subjecting a compound represented by the general formula:

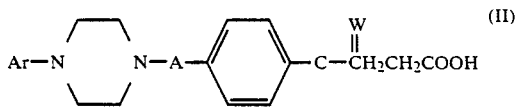 (II)

wherein C=W represents C=O or C=NOH; and other symbols have the same definitions as above, to reduction and cyclization reactions. Accordingly, the compounds of the general formula (I) of the present invention can be produced by the methods described below.

(1a) Of the compounds of the general formula (I), a compound having —O— for Z can be produced by cyclizing a compound represented by the general formula:

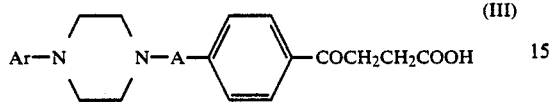

wherein the symbols have the same definitions as above, after reduction.

The starting compound is reduced in an appropriate solvent with a reducing agent at 0° to 100° C. for 5 minutes to 5 hours, whereafter the resulting alcohol compound, without being purified, is cyclized in an appropriate solvent in the presence of acid at 0° to 100° C. for 5 minutes to 5 hours, whereby the desired compound is produced.

Any solvent can be used for the reduction reaction, as long as it does not interfere with the reaction. Usable solvents include methanol, ethanol, isopropanol, tetrahydrofuran and dioxane. Usable reducing agents include metal hydrides such as sodium borohydride and sodium cyanoborohydride. The purpose of reduction may also be accomplished by catalytic reduction in the presence of palladium carbon, Raney nickel, etc. as the catalyst. Also, any solvent can be used for the cyclization reaction, as long as it does not interfere with the reaction. Usable solvents include methanol, ethanol, isopropanol, tetrahydrofuran and dioxane. The acid can be chosen as appropriate from inorganic acids such as hydrochloric acid and sulfuric acid or organic acids such as acetic acid and p-toluenesulfonic acid.

(1b) Of the compounds of the general formula (I), a compound having —NH— for Z can be produced by reductively cyclizing a compound represented by the general formula:

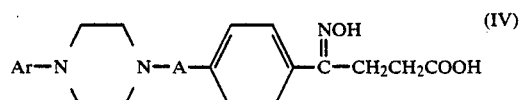

wherein the symbols have the same definitions as above.

The reaction is carried out in an appropriate solvent in the presence of catalyst by hydrogenation at 100° to 150° C. in an autoclave followed by heating at the same temperature for 1 to 10 hours. For the solvent, an alcohol solvent such as methanol or ethanol is used. For the catalyst, palladium carbon, Raney nickel, etc. can be used.

(2) Of the compounds of the general formula (I), a compound having —NR— for Z can be produced by reaction between a compound represented by the general formula:

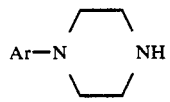

wherein Ar has the same definition as above and a compound represented by the general formula:

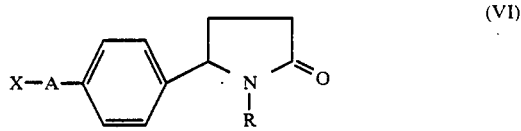

wherein X represents halogen or reactive alcohol derivative (e.g. p-toluenesulfonyloxy, methanesulfonyloxy) and the other symbols have the same definitions as above.

The reaction is carried out in an appropriate solvent in the presence of a deacidifying agent by heating at 50° to 150° C. for 5 to 24 hours. For the solvent, solvents which do not interfere with the reaction such as benzene, toluene, ethanol, isopropanol, N,N-dimethylacetamide and N,N-dimethylformamide can be used singly or in combination. The deacidifying agent can be chosen as appropriate from potassium carbonate, sodium hydrogencarbonate, triethylamine, pyridine, etc.

Of the compounds of the general formula (I), a compound having —NR'— for Z wherein R' represents any one of the groups for R other than hydrogen can be produced by Method 3, 4 or 5 described below.

(3) The method in which a compound having —NH— for Z produced by Method 1b and a compound represented by the general formula:

wherein $R^5$ represents lower alkyl or aralkyl and Y represents halogen, are reacted together.

The reaction is carried out in an appropriate solvent in the presence of a base for 1 to 24 hours while cooling or while refluxing the solvent used. The solvent can be chosen as appropriate from acetone, methyl ethyl ketone, benzene, toluene, N,N-dimethylformamide, hexamethylphosphoramide, tetrahydrofuran and dioxane. The base can be chosen as appropriate from triethylamine, potassium carbonate, sodium hydroxide, sodium alcoholate, sodium hydride, etc.

(4) The method in which a compound having —O— for Z produced by Method (1a) and an amine represented by the general formula:

wherein $R^6$ represents lower alkyl, aralkyl, aryl or a group of the formula (a) are reacted together.

The reaction is carried out in an appropriate solvent by heating at 100° to 150° C. in an autoclave for 5 to 24 hours.

For the solvent, any solvent can be used, as long as it does not interfere with the reaction. Usable solvents include methanol, ethanol, isopropanol, benzene and toluene.

(5) The method in which the starting compound (III) used in Method (1a) and the amine of formula (VIII) are reductively cyclized together.

The reaction is carried out in an appropriate solvent in the presence of catalyst by heating at 100° to 150° C. in hydrogen gas in an autoclave.

For the solvent, an alcohol solvent such as methanol or ethanol is used. For the catalyst, palladium carbon, Raney nickel, etc. can be used.

(6) Of the compounds of the general formula (I), a compound having —N(COR$^7$)— for Z wherein R$^7$ represents lower alkyl, aryl or aralkyl can be produced by reaction between a compound having —NH— for Z produced by Method (1b) and a compound represented by the general formula:

$$R^7COY \qquad (IX)$$

wherein the symbols have the same definitions as above.

The reaction is carried out in an appropriate solvent in the presence of a deacidifying agent for 1 to 24 hours while cooling or while refluxing the solvent used.

For the solvent, any solvent which does not interfere with the reaction, such as chloroform, benzene, toluene, tetrahydrofuran or N,N-dimethylformamide can be used. The deacidifying agent can be chosen as appropriate from triethylamine, pyridine, potassium carbonate, etc.

(7) Of the compounds of the general formula (I), a compound having —N(CONHR$^3$)— for Z can be produced by reacting a compound having —NH— for Z produced by Method (2) with an isocyanate represented by the general formula:

$$R^3NCO \qquad (X)$$

wherein R$^3$ has the same definition as above.

The reaction is carried out in an appropriate solvent by heating at 0° to 100° C. for 1 to 24 hours.

For the solvent, any solvent which does not interfere with the reaction, such as chloroform, benzene, toluene or tetrahydrofuran, can be used.

The compound of the general formula (I) thus obtained, if desired, may be converted to a pharmaceutically acceptable acid addition salt by treating with an inorganic acid such as hydrochloric acid, hydrobromic acid, sulfuric acid or phosphoric acid or an organic acid such as maleic acid, fumaric acid, citric acid, methanesulfonic acid, tartatic acid or pamoic acid.

Having 1 or 2 chiral carbons, the compounds (I) of the present invention can be obtained as a racemic mixture or diastereomer mixture, and the present invention embraces the individual optical isomers thereof.

The compounds of the general formulae (III) and (IV) are new compounds, and can be produced by Methods (i) and (ii) described below, for instance.

(i) The method in which reaction is carried out between a compound represented by the general formula:

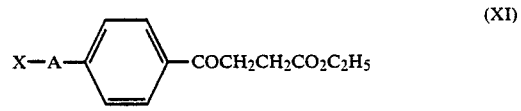

(XI)

wherein the symbols have the same definitions as above and a compound of the general formula (V), followed by hydrolysis.

The reaction is carried out by heating at 50° to 150° C. for 5 to 24 hours in an appropriate solvent in the presence of a deacidifying agent, and hydrolyzing the resulting ester compound in an appropriate solvent with sodium hydroxide for 30 minutes to 5 hours while refluxing the solvent used.

For the first reaction, solvents which do not interfere with the reaction can be used singly or in combination, such as benzene, toluene, ethanol, isopropanol, N,N-dimethylacetamide and N,N-dimethylformamide, and the deacidifying agent can be chosen as appropriate from potassium carbonate, sodium hydrogencarbonate, triethylamine, pyridine, etc. For the solvent used in the hydrolysis, water can be used singly or in combination with ethanol, tetrahydrofuran, dioxane, dimethylformamide, etc.

(ii) The method in which the compound of the general formula (III) obtained by Method (i) described above is converted to an oxime by reaction with hydroxylamine hydrochloride.

The reaction is carried out in an appropriate solvent in the presence of a deacidifying agent by heating for 1 to 24 hours while refluxing the solvent used. Any solvent which does not interfere with the reaction can be used, such as methanol, ethanol, isopropanol, tetrahydrofuran or dioxane. The deacidifying agent can be chosen as appropriate from potassium carbonate, sodium hydrogencarbonate, triethylamine, and the like.

ACTION AND EFFECT OF THE INVENTION

The compounds of the present invention possessed necessary pharmacological activities as neuroleptics such as depressive action of spontaneous motility, anti-apomorphine action, methamphetamine-antagonistic action or potentiating action of tetrabenazine-induced blepharoptosis, and further exhibited particularly potential inhibitory action on serotonin-induced head-twitch. In determining the affinity for various receptors with tritium-labeled ligands, the compounds of the present invention showed a high affinity for the serotonin receptor rather than the dopamine and norepinephrine receptors.

Moreover, the compounds of the present invention are useful as neuroleptics with less extrapyramidal side effects since they showed very weak cataleptogenic action in the studies of such action in rats as the index of the extrapyramidal side effects.

The pharmacological features of the compounds of the present invention are exemplified as follows:

Experiment 1 Anti-apomorphine action

Groups of 3 male dd-strain mice (4 groups/dose) were used. Test compounds were orally administered and an hour later, 0.5 mg/kg of apomorphine was subcutaneously administered. Immediately thereafter, motility was measured with the aid of Varimex (manufactured by Columbus Co.) for 20 minutes. The ED$_{50}$ values, the dose of test compound required to lower the motility of the control group by 50%, were graphically calculated.

Experiment 2 Anti-serotonin action (head-twitch method in mice)

Groups of 8–30 male dd-strain mice were used. The test compounds were orally administered and an hour later, 40 μg/0.02 ml of serotonin was intracerebroventricularly administered. Ten minutes thereafter, the numbers of head-twitch were measured for 5 minutes. The ED$_{50}$ values calculated by the probit method considering the number of head-twitch induced by the administration of serotonin with less than once as the inhibitory action by the test compound.

Experiment 3 Affinity for serotonin receptor (1) Affinity for serotonin-1 receptor: $^3$H-8-hydroxy-2-(dipropylamino)tetralin($^3$H-8-OH-DPAT) binding assay Preparation of synaptosomal membranes and $^3$H-8-OH-DPAT binding assay were performed according to the method of Hall et al(Journal of Neurochemistry, vol. 44, p. 1685, 1985).

Rat hyppocampus which was maintained in a freezed state was homogenized in 40-fold volumes of ice-cold 50 mM Tris-HCl buffer (pH 7.4) and centrifugated at 500 g for 10 minutes at 0° C. Further, the supernatant was centrifugated at 40,000 g for 20 minutes at 0° C. and the pellets thus obtained were homogenized in 40-fold volumes of the same buffer as mentioned above, and then incubated at 37° C. for 10 minutes. After incubation, the suspension was centrifugated at 40,000 g for 20 minutes at 0° C. The obtained pellets were washed by repeating twice the procedures of homogenization in the above-mentioned buffer and centrifugation. The suspension of synaptosomal membranes was prepared by homogenizing the pellets finally obtained in 60-fold volumes of 50 mM Tris-HCl buffer (pH 7.4) containing 1 mM manganese chloride.

To 900 µl of the membrane suspension were added 50 µl of $^3$H-8-OH-DPAT solution (final concentration: 0.2 nM), and 50 µl of the test compound solution or the solvent and the mixture was incubated at 37° C. for 10 minutes. After incubation, 5 ml of ice-cold 50 mM Tris-HCl buffer (pH 7.4) was added, and immediately thereafter, the mixture was filtered with suction through Whatman GF/B filter. The filter was washed twice with 5 ml of the same buffer as mentioned above and the radioactivity on the filter was measured by a liquid scintillation counter.

(2) Affinity for serotonin-2 receptor: $^3$H-spiperone bindig assay

The preparation of synaptosomal membranes and binding assay were performed according to the method of Peroutka and Snyder (Molecular Pharmacology, vol. 16, p. 687, 1979).

Rat cerebral cortex which was maintained in a freezed state was homogenized in 20-fold volumes of ice-cold 0.32 M sucrose and centrifugated at 1,000 g for 10 minutes at 0° C. The supernatant was centrifugated at 50,000 g for 15 minutes at 0° C. The obtained pellets were homogenized in 20-fold volumes of ice-cold 50 mM Tris-HCl buffer (pH 7.5). The mixture was incubated at 37° C. for 10 minutes, and further centrifugated at 50,000 g for 15 minutes at 0° C. The suspension of synaptosomal membrane was prepared by homogenizing the obtained pellets in 60-fold volumes of the buffer mentioned above containing 1.1 mM ascorbic acid, 4 mM calcium chloride and 10 µM pargyline.

To 900 µl of the suspension of synaptosomal membrane were added 50 µl of $^3$H-spiperone (final concentration : 0.5 nM) and 50 µl of the test compound solution or the solvent, and then incubated at 37° C. for 20 minutes. After the completion of incubation, 5 ml of ice-cold buffer as mentioned above was added. Immediately thereafter, the mixture was filtered with suction through Whatman GF/B filter. The filter was washed twice with 5 ml of the same buffer as mentioned above and the radioactivity on the filter was measured by a liquid scintillation counter.

The results of the above experiments are summarized in the following Table 1.

Then, the cataleptogenic action of the compound of Example 15 was studied for the purpose of measuring the degree of the extrapyramidal side effect.

TABLE 1

| | Anti-apomorphine action $ED_{50}$ (mg/kg, p.o.) | Anti-serotonin action $ED_{50}$ (mg/kg, p.o.) | Affinity for receptor | |
|---|---|---|---|---|
| | | | Serotonin-1 Ki (M) | Serotonin-2 Ki (M) |
| Compound of Example 1 | 13 | 0.53 | $6.1 \times 10^{-10}$ | $2.3 \times 10^{-8}$ |
| Compound of Example 2 | 15 | 0.15 | $3.1 \times 10^{-10}$ | $7.8 \times 10^{-8}$ |
| Compound of Example 6 | 4.2 | 2.2 | $4.7 \times 10^{-9}$ | $6.6 \times 10^{-8}$ |
| Compound of Example 7 | 2.1 | 3.5 | $2.8 \times 10^{-10}$ | $4.8 \times 10^{-7}$ |
| Compound of Example 9 | 9.5 | 2.4 | $4.5 \times 10^{-9}$ | $2.5 \times 10^{-7}$ |
| Compound of Example 15 | 4.2 | 0.32 | $4.0 \times 10^{-10}$ | $6.3 \times 10^{-8}$ |

Experiment 4 Cataleptogenic action

Groups of 10 female Wistar-strain rats were used. Catalepsy was measured by the partly modified method of Simon et al (Journal of Pharmacy and Pharmacology, vol. 22, P. 546, 1970). The front paws of the rats were placed gently on a vertical grid (4 mm diameter, 9 cm height). It was considered cataleptic if the rat did not move more than a minute.

After the compound of Example 15 was orally administered, catalepsy was measured with the passage of time in 9 hours. The $ED_{50}$ values were calculated from the number of catalepsy-positive animals at the peak time of catalepsy by the probit method, and the test compound showed very weak cataleptic action, i.e. $ED_{50}$ value was 250 mg/kg.

All mice survived even by orally administered 300 mg/kg of the compounds of the present invention.

The compounds of the present invention, when used as drugs, can be safely administered to a patient in the form of tablets, powders, granules, capsules, injection, infusion drips, etc. usually in combination with a carrier, excipient, diluent and/or solubilizer. Although dosage amount may vary with the symptoms, body weight, age and other factors of the patient, the compound is usually administered in the dose range of from 1 to 500 mg for each adult daily at a frequency of 1 to several times a day.

Formulation example for pharmaceutical preparation:

A tablet containing 5 mg of the compound may have the following composition:

| | |
|---|---|
| Compound of Example 15 | 5 mg |
| Lactose | 79.4 mg |
| Corn starch | 20 mg |
| Crystalline cellulose | 15 mg |
| Magnesium stearate | 0.6 mg |
| Total | 120 mg |

EXAMPLES

The present invention will now be described in more detail by means of the following working examples and reference examples, but the present invention is not limited thereto.

EXAMPLE 1

To 9.7 g of 4-hydroxyimino-4-[4-(4-(4-(3-methylphenyl)piperazin-1-yl)butyl)phenyl]butyric acid and 5 g of Raney nickel, 300 ml of methanol is added, and stirred for 9 hours in 70 atm hydrogen gas at 120° C. in an autoclave. After the completion of the reaction, the catalyst is removed by filtration, and the solvent is distilled off under reduced pressure. The resulting oily substance is purified by silica gel column chromatography and recrystallized from ethyl acetate to give 6.4 g of 5-[4-(4-(4-(3-methylphenyl)piperazin-1-yl)butyl)phenyl]pyrrolidin-2-one having a melting point of 114° to 116° C.

EXAMPLE 2

To 5.9 g of 4-hydroxyimino-4-[4-(2-(4-(3-trifluoromethylphenyl)piperazin-1-yl)ethyl)phenyl]butyric acid and 5 g of Raney nickel, 200 ml of methanol is added, and stirred for 9 hours in 80 atm hydrogen gas at 110° C. in an autoclave. After the completion of the reaction, the catalyst is removed by filtration, and the solvent is distilled off under reduced pressure. The resulting oily substance is purified by silica gel column chromatography, after which it is converted to hydrochloride by means of a 25% hydrogen chloride-isopropanol solution. The resulting crystal is further recrystallized from isopropanol to give 1.1 g of 5-[4-(2-(4-(3-trifluoromethylphenyl)piperazin-1-yl)ethyl)phenyl]pyrrolidin-2-one hydrochloride having a melting point of 212° C.

EXAMPLE 3

To 4.6 g of 4-hydroxyimino-4-[4-(3-(4-(3-trifluoromethylphenyl)piperazin-1-yl)propyl)phenyl]butyric acid and 5 g of Raney nickel, 300 ml of methanol is added, and stirred for 9 hours in 80 atm hydrogen gas at 130° C. in an autoclave. After the completion of the reaction, the catalyst is removed by filtration, and the solvent is distilled off under reduced pressure. The resulting oily substance is dissolved in isopropanol and converted to the fumarate by means of fumaric acid. The resulting crystal is further recrystallized from isopropanol to give 1.0 g of 5-[4-(3-(4-(3-trifluoromethylphenyl)piperazin-1-yl)propyl)phenyl]pyrrolidin-2-one fumarate having a melting point of 184° to 186° C.

EXAMPLE 4

Using 4-hydroxyimino-4-[4-(4-(4-(4-methylphenyl)piperazin-1-yl)butyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(4-(4-(4-methylphenyl)piperazin-1-yl)butyl)phenyl]pyrrolidin-2-one having a melting point of 164° to 165° C.

EXAMPLE 5

Using 4-hydroxyimino-4-[4-(4-(4-(2,3-dimethylphenyl)piperazin-1-yl)butyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(4-(4-(2,3-dimethylphenyl)piperazin-1-yl)butyl)phenyl]pyrrolidin-2-one having a melting point of 112° to 114° C.

EXAMPLE 6

Using 4-hydroxyimino-4-[4-(4-(4-(4-fluorophenyl)piperazin-1-yl)butyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(4-(4-(4-fluorophenyl)piperazin-1-yl)butyl)phenyl]pyrrolidin-2-one having a melting point of 136° to 137° C.

Example 7

Using 4-hydroxyimino-4-[4-(4-(4-(2-methoxyphenyl)piperazin-1-yl)butyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(4-(4-(2-methoxyphenyl)piperazin-1-yl)butyl)phenyl]pyrrolidin-2-one having a melting point of 130° to 131° C.

EXAMPLE 8

Using 4-hydroxyimino-4-[4-(4-(4-(4-methoxyphenyl)piperazin-1-yl)butyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(4-(4-(4-methoxyphenyl)piperazin-1-yl)butyl)phenyl]pyrrolidin-2-one having a melting point of 155° to 156° C.

EXAMPLE 9

Using 4-hydroxyimino-4-[4-(3-(4-phenylpiperazin-1-yl)propyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(3-(4-phenylpiperazin-1-yl)propyl)phenyl]pyrrolidin-2-one having a melting point of 130° C.

EXAMPLE 10

Using 4-hydroxyimino-4-[4-(3-(4-(3-methylphenyl)piperazin-1-yl)propyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(3-(4-(3-methylphenyl)piperazin-1-yl)propyl)phenyl]pyrrolidin-2-one having a melting point of 87° to 89° C.

EXAMPLE 11

Using 4-hydroxyimino-4-[4-(3-(4-(4-methylphenyl)piperazin-1-yl)propyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(3-(4-(4-methylphenyl)piperazin-1-yl)propyl)phenyl]pyrrolidin-2-one having a melting point of 143° to 145° C.

EXAMPLE 12

Using 4-hydroxyimino-4-[4-(3-(4-(2-methoxyphenyl)piperazin-1-yl)propyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(3-(4-(2-methoxyphenyl)piperazin-1-yl)propyl)phenyl]pyrrolidin-2-one having a melting point of 109° to 111° C.

EXAMPLE 13

Using 4-hydroxyimino-4-[4-(2-(4-(2-pyrimidinyl)piperazin-1-yl)ethyl)phenyl]butyric acid in place of 4-hydroxyimino-4-[4-(4-(4-(3-methylphenyl)piperazin-1-

EXAMPLE 14

Using 4-hydroxyimino-4-[4-(4-(4-phenylpiperazin-1-yl)buthyl)phenyl]butyric acid in place of 4-hydroxyimino-4-[4-(2-(4-(3-trifluoromethylphenyl)piperazin-1-yl)ethyl)phenyl]butyric acid of Example 2, reaction is carried out in the same manner to give 5-[4-(4-(4-phenylpiperazin-1-yl)butyl)phenyl]pyrrolidin-2-one dihydrochloride having a melting point of 236° to 239° C.

EXAMPLE 15

Using 4-hydroxyimino-4-[4-(4-(4-(3-trifluoromethylphenyl)piperazin-1-yl)butyl)phenyl]butyric acid in place of 4-hydroxyimino-4-[4-(2-(4-(3-trifluoromethylphenyl)piperazin-1-yl)ethyl)phenyl]butyric acid of Example 2, reaction is carried out in the same manner to give 5-[4-(4-(4-(3-trifluoromethylphenyl)piperazin-1-yl)butyl)phenyl]pyrrolidin-2-one dihydrochloride having a melting point of 176° to 179° C. with decomposition.

EXAMPLE 16

Using 4-hydroxyimino-4-[4-(4-(4-(2-methylphenyl)piperazin-1-yl)butyl)phenyl]butyric acid in place of 4-hydroxyimino-4-[4-(2-(4-(3-trifluoromethylphenyl)piperazin-1-yl)ethyl)phenyl]butyric acid of Example 2, reaction is carried out in the same manner to give 5-[4-(4-(4-(2-methylphenyl)piperazin-1-yl)butyl)phenyl]pyrrolidin-2-one dihydrochloride ¼ hydrate having a melting point of 215° to 218° with decomposition.

EXAMPLE 17

To 4.4 g of 4-oxo-4-[4-(4-(4-phenylpiperazin-1-yl)butyl)phenyl]butyric acid, 150 ml of methanol is added. To this mixture, 4.0 g of sodium borohydride is added under cooling, and stirred for 3 hours. After the completion of the reaction, the reaction liquid is concentrated under reduced pressure. After neutralization with dilute hydrochloric acid, the concentrate is extracted with chloroform and dried over anhydrous magnesium sulfate, and the solvent is distilled off under reduced pressure. The residue is purified by silica gel chromatography, after which it is dissolved in 50 ml of isopropanol. To the resulting solution, 3.5 ml of a 25% hydrogen chloride-isopropanol solution is added. This mixture, after being kept standing at room temperature for 30 minutes, is concentrated under reduced pressure. After cooling, the crystals which have precipitated are collected by filtration and further recrystallized from isopropanol to give 2.2 g of 5-[4-(4-(4-phenylpiperazin-1-yl)butyl)phenyl]tetrahydrofuran-2-one dihydrochloride having a melting point of 205° to 206° C. with decomposition.

EXAMPLE 18

Using 4-oxo-4-[4-(4-(4-(3-trifluoromethylphenyl)piperazin-1-yl)butyl)phenyl]butyric acid in place of 4-oxo-4-[4-(4-(4-phenylpiperazin-1-yl)butyl)phenyl]butyric acid of Example 17, reaction is carried out in the same manner to give 5-[4-(4-(4-(3-trifluoromethylphenyl)piperazin-1-yl)butyl)phenyl]tetrahydrofuran-2-one hydrochloride ¼ hydrate having a melting point of 194° to 196° C. with decomposition.

EXAMPLE 19

Using 4-oxo-4-[4-(4-(4-(2,3-dimethylphenyl)piperazin-1-yl)butyl)phenyl]butyric acid in place of 4-oxo-4-[4-(4-(4-phenylpiperazin-1-yl)butyl)phenyl]butyric acid of Example 17, reaction is carried out in the same manner to give 5-[4-(4-(4-(2,3-dimethylphenyl)piperazin-1-yl)butyl)phenyl]tetrahydrofuran-2-one hydrochloride ½ hydrate having a melting point of 225° to 228° C. with decomposition.

EXAMPLE 20

Using 4-oxo-4-[4-(4-(4-(3-chlorophenyl)piperazin-1-yl)butyl)phenyl]butyric acid in place of 4-oxo-4-[4-(4-(4-phenylpiperazin-1-yl)butyl)phenyl]butyric acid of Example 17, reaction is carried out in the same manner to give 5-[4-(4-(4-(3-chlorophenyl)piperazin-1-yl)butyl)phenyl]tetrahydrofuran-2-one hydrochloride having a melting point of 155° to 156° C. with decomposition.

EXAMPLE 21

Using 4-oxo-4-[4-(3-(4-phenylpiperazin-1-yl)propyl)phenyl]butyric acid in place of 4-oxo-4-[4-(4-(4-phenylpiperazin-1-yl)butyl)phenyl]butyric acid of Example 17, reaction is carried out in the same manner to give 5-[4-(3-(4-phenylpiperazin-1-yl)propyl)phenyl]tetrahydrofuran-2-one hydrochloride having a melting point of 207° to 208° C. with decomposition.

EXAMPLE 22

3.7 g of 5-[4-(3-(4-phenylpiperazin-1-yl)propyl)phenyl]pyrrolidin-2-one as produced in Example 9 is added to 37 ml of chloroform and 1.5 g of triethylamine. While cooling and stirring the mixture, 1.2 g of acetyl chloride is added dropwise, and stirred for 3 more hours at room temperature. After the completion of the reaction, the reaction liquid is washed with water and dried over anhydrous magnesium sulfate, and the solvent is distilled off under reduced pressure. The residue is purified by silica gel column chromatography, after which it is converted to the hydrochloride by means of a 25% hydrogen chloride-isopropanol solution. The resulting crystals are further recrystallized from isopropanol-isopropyl ether to give 2.3 g of N-acetyl-5-[4-(3-(4-phenylpiperazin-1-yl)propyl)phenyl]pyrrolidin-2-one hydrochloride monohydrate having a melting point of 119° to 120° C.

EXAMPLE 23

To 3 g of 5-[4-(4-(4-(3-trifluoromethylphenyl)piperazin-1-yl)butyl)phenyl]pyrrolidin-2-one hydrochloride as produced in Example 15, 100 ml of toluene, 1 ml of ethyl isocyanate and 2 ml of triethylamine are added, and stirred for 10 hours at 70° to 80° C. After the completion of the reaction, the solvent is distilled off under reduced pressure. The residue is purified by silica gel column chromatography, after which it is converted to the hydrochloride by means of a 25% hydrogen chloride-isopropanol solution. The resulting crystals are further recrystallized from ethanol to give 1,1 g of N-ethylcarbamoyl-5-[4-(4-(4-(3-trifluoromethylphenyl)piperazin-1-yl)butyl)phenyl]pyrrolidin-2-one hydrochloride having a melting point of 178° to 182° C. with decomposition.

EXAMPLE 24

Using 4-hydroxyimino-4-[4-(4-(4-(2-pyrimidinyl)piperazin-1-yl)butyl)phenyl]butyric acid in place of 4- hydroxyimino-4-[4-(4-(4-(3-methylphenyl)piperazin-1-yl)butyl)phenyl]butyric acid of Example 1, reaction is carried out in the same manner to give 5-[4-(4-(4-(2-pyrimidinyl)piperazin-1-yl)butyl)phenyl]pyrrolidin-2-one.

EXAMPLE 25

Using 4-hydroxyimino-4-[4-(2-(4-(3-methylphenyl)piperazin-1-yl)ethyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(2-(4-(3-methylphenyl)piperazin-1-yl)ethyl)phenyl]pyrrolidin-2-one.

EXAMPLE 26

Using 4-hydroxyimino-4-[4-(2-(4-(4-fluorophenyl)piperazin-1-yl)ethyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(2-(4-(4-fluorophenyl)piperazin-1-yl)ethyl)phenyl]pyrrolidin-2-one.

EXAMPLE 27

Using 4-hydroxyimino-4-[4-(4-(4-(6-methylpyridin-2-yl)piperazin-1-yl)butyl)phenyl]butyric acid in place of 4-hydroxyimino-4-[4-(4-(4-(3-methylphenyl)piperazin-1-yl) butyl)phenyl]butyric acid of Example 1, reaction is carried out in the same manner to give 5-[4-(4-(4-(6-methylpyridin-2-yl)piperazin-1-yl)butyl)phenyl ]pyrrolidin-2-one.

EXAMPLE 28

Using 4-hydroxyimino-4-[4-(2-methyl-2-(4-(3-trifluoromethylphenyl)piperazin-1-yl)ethyl)phenyl]-butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(2-methyl-2-(4-(3-trifluoromethylphenyl)-piperazin-1-yl)ethyl)phenyl]pyrrolidin-2-one.

EXAMPLE 29

Using 4-hydroxyimino-4-[4-(2-methyl-3-(4-(3-trifluoromethylphenyl)piperazin-1-yl)propyl)phenyl]-butyric acid in place of 4-hydroxyimino-4-[4-(4-(4-(3-methylphenyl)piperazin-1yl)butyl)phenyl]butyric acid of Example 1, reaction is carried out in the same manner to give 5-[4-(2-methyl-3-(4-(3-trifluoromethylphenyl)-piperazin-1-yl)propyl)phenyl]pyrrolidin-2-one.

EXAMPLE 30

Using 4-hydroxyimino-4-[4-(2-methyl-3-(4-(3-methylphenyl)piperazin-1-yl)propyl)phenyl]butyric acid in place of 4-hydroxyimino-4-[4-(4-(4-(3-methylphenyl)piperazin-1-yl)butyl)phenyl]butyric acid of Example 1, reaction is carried out in the same manner to give 5-[4-(2-methyl-3-(4-(3-methylphenyl)piperazin-1-yl)propyl)phenyl ]pyrrolidin-2-one.

EXAMPLE 31

4-Oxo-4-[4-(4-(4-(3-trifluoromethylphenyl)piperazin-1-yl)butyl)phenyl]butyric acid and ethylamine are reacted together to give N-ethyl-5-[4-(4-(4-(3-trifluoromethylphenyl)piperazin-1-yl)butyl)phenyl ]pyrrolidin-2-one.

EXAMPLE 32

4-Oxo-4-[4-(4-(4-(4-methylphenyl)piperazin-1-yl)butyl)phenyl]butyric acid and methylamine are reacted together to give N-methyl-5-[4-(4-(4-(4-methylphenyl)piperazin-1-yl)butyl)phenyl]pyrrolidin-2-one.

EXAMPLE 33

4-Oxo-4-[4-(3-(4-(3-methylphenyl)piperazin-1-yl)propyl)phenyl]butyric acid and ethylamine are reacted together to give N-ethyl-5-[4-(3-(4-(3-methylphenyl)piperazin-1-yl)propyl)phenyl]pyrrolidin-2-one.

EXAMPLE 34

4-Oxo-4-[4-(2-(4-(2-pyrimidinyl)piperazin-1-yl)ethyl)phenyl]butyric acid and methylamine are reacted together to give N-methyl-5-[4-(2-(4-(2-pyrimidinyl)-piperazin-1-yl)etheyl)phenyl]pyrrolidin-2-one.

EXAMPLE 35

4-Oxo-4-[4-(4-(4-(3-trifluoromethylphenyl)piperazin-1-yl)butyl)phenyl]butyric acid and benzylamine are reacted together to give N-benzyl-5-[4-(4-(4-(3-trifluoromethylphenyl)piperazin-1-yl)butyl)phenyl ]pyrrolidin-2-one.

EXAMPLE 36

4-Oxo-4-[4-(3-(4-(3-methylphenyl)piperazin-1-yl)propyl)phenyl]butyric acid and aniline are reacted together to give N-phenyl-5-[4-(3-(4-(3-methylphenyl)-piperazin-1-yl)propyl)phenyl]pyrrolidin-2-one.

EXAMPLE 37

5-[4-(4-(4-(3-Trifluoromethylphenyl)piperazin-1-yl)butyl)phenyl]pyrrolidin-2-one as obtained in Example 15 and phenylacetyl chloride are reacted together in the same manner as in Example 22 to give N-phenylacetyl-5-[4-(4-(4-(3-trifluoromethylphenyl)piperazin-1-yl)butyl)phenyl]pyrrolidin-2-one.

EXAMPLE 38

5-[4-(2-(4-(3-Trifluoromethylphenyl)piperazin-1-yl)butyl)phenyl]pyrrolidin-2-one as obtained in Example 2 and benzoyl chloride are reacted together in the same manner as in Example 22 to give N-benzoyl-5-[4-(2-(4-(3-trifluoromethylphenyl)piperazin-1-yl)ethyl)-phenyl]pyrrolidin-2-one.

EXAMPLE 39

5-[4-(4-(4-(2-Pyrimidinyl)piperazin-1-yl)butyl)phenyl ]pyrrolidin-2-one as obtained in Example 24 and acetyl chloride are reacted together in the same manner as in Example 22 to give N-acetyl-5-[4-(4-(4-(2-pyrimidinyl)-piperazin-1-yl)butyl)phenyl]pyrrolidin-2-one.

EXAMPLE 40

5-[4-(2-(4-(3-Methylphenyl)piperazin-1-yl)ethyl)-phenyl]pyrrolidin-1-one as obtained in Example 25 and ethyl isocyanate are reacted together in the same manner as in Example 23 to give N-ethylcarbamoyl-5-[4-(2-(4-(3-methylphenyl)piperazin-1-yl)ethyl)phenyl]pyrrolidin-1-one.

EXAMPLE 41

5-[4-(3-(4-(4-Methylphenyl)piperazin-1-yl)propyl)-phenyl]pyrrolidin-2-one as obtained in Example 11 and phenyl isocyanate are reacted together in the same manner as in Example 23 to give N-phenylcarbamoyl-5-[4-

(3-(4-(4-methylphenyl)piperazin-1-yl)propyl)phenyl]pyrrolidin-2-one.

EXAMPLE 42

5-[4-(4-(4-(2-Methoxyphenyl)piperazin-1-yl)butyl)phenyl]pyrrolidin-2-one as obtained in Example 7 and allyl isocyanate are reacted together in the same manner as in Example 23 to give N-allylcarbamoyl-5-[4-(4-(4-2-methoxyphenyl)piperazin-1-yl)butyl)phenyl]pyrrolidin-2-one.

EXAMPLE 43

Using 4-oxo-4-[4-(4-(4-(4-methoxyphenyl)piperazin-1yl)butyl)phenyl]butyric acid in place of 4-oxo-4-[4-(4-(4-phenylpiperazin-1-yl)butyl)phenyl]butyric acid of Example 17, reaction is carried out in the same manner to give 5-[4-(4-(4-(4-methoxyphenyl)piperazin-1-yl)butyl)phenyl]tetrahydrofuran-2-one.

EXAMPLE 44

Using 4-oxo-4-[4-(4-(4-(3-methylphenyl)piperazin-1yl)butyl)phenyl]butyric acid in place of 4-oxo-4-[4-(4-(4-(4 phenylpiperazin-1-yl)butyl)phenyl]butyric acid of Example 17, reaction is carried out in the same manner to give 5-[4-(4-(4-(3-methylphenyl)piperazin-1-yl)butyl)phenyl]tetrahydrofuran-2-one.

EXAMPLE 45

Using 4-oxo-4-[4-(2-(4-(2-pyrimidinyl)piperazin-1-yl)ethyl)phenyl]butyric acid in place of 4-oxo-4-[4-(4-(4-phenylpiperazin-1-yl)butyl)phenyl]butyric acid of Example 17, reaction is carried out in the same manner to give 5-[4-(2-(4-(2-pyrimidinyl)piperazin-1-yl)ethyl)phenyl]tetrahydrofuran-2-one.

EXAMPLE 46

Using 4-oxo-4-[4-(3-(4-(4-methylphenyl)piperazin-1-yl)propyl)phenyl]butyric acid in place of 4-oxo-4-[4-(4-(4-phenylpiperazin-1-yl)butyl)phenyl]butyric acid of Example 17, reaction is carried out in the same manner to give 5-[4-(3-(4-(4-methylphenyl)piperazin-1-yl)propyl)phenyl]tetrahydrofuran-2-one.

EXAMPLE 47

5-[4-(4-(p-Toluenesulfonyloxy)butyl)phenyl]pyrrolidin-2-one and 1-(3-chlorophenyl)piperazine are reacted together to give 5-[4-(4-(4-(3-chlorophenyl)piperazin-1-yl)butyl)phenyl]-pyrrolidin-2-one.

EXAMPLE 48

Using 1-(3-cyanopyridin-2-yl)piperazine in place of 1-(3-chlorophenyl)piperazine of Example 47, reaction is carried out in the same manner to give 5-[4-(4-(4-(3-cyanopyridin-2-yl)piperazin-1-yl)butyl)phenyl]pyrrolidin-2-one.

EXAMPLE 49

N-(3-morpholinopropyl)-5-[4-(4-(p-toluenesulfonyloxy)butyl)phenyl]pyrrolidin-2-one and 1-(3-trifluoromethylphenyl)piperazine are reacted together to give N-(3-morpholinopropyl)-5-[4-(4-(4-(3-trifluoromethylphenyl)piperazin-1-yl)butyl)phenyl]pyrrolidin-2-one.

EXAMPLE 50

N-(2-(N,N-diethylamino)ethyl)-5-[4-(4-(p-toluenesulfonyloxy)butyl)phenyl]pyrrolidin-2-one and 1-(3-methylphenyl)piperazine are reacted together to give N-(2-(N,N-diethylamino)ethyl)-5-[4-(4-(4-(3-methylphenyl)piperazin-1-yl)butyl)phenyl]pyrrolidin-2-one.

REFERENCE EXAMPLE 1

20 g of ethyl 4-oxo-4-[4-(4-chlorobutyl)phenyl]butyrate and 12 g of 1-(3-methylphenyl)piperazine are dissolved in a mixed solvent of 80 ml of dimethylformamide and 80 ml of toluene. To this solution, 14 g of potassium carbonate is added, and this is followed by reflux with heating for 18 hours under stirring the solution. After the completion of the reaction, the reaction liquid is concentrated under reduced pressure and extracted with ethyl acetate. After being washed with water, the extract is dried over anhydrous magnesium sulfate, and the solvent is distilled off under reduced pressure. The resulting oily substance is purified by silica gel column chromatography, after which it is crystallized with isopropyl ether to give 17.2 g of ethyl 4-oxo-4-[4-(4-(4-(3-methylphenyl)piperazin-1-yl)butyl)phenyl ]butyrate having a melting point of 62° to 63° C.

This ester is then dissolved in 200 ml of ethanol. To this solution, a solution of 4.7 g of sodium hydroxide in 20 ml of water is added, and this is followed by reflux with heating for 30 minutes. After the completion of the reaction, the solvent is distilled off, and the residue, after dilution with water, is adjusted to pH 5 with hydrochloric acid. The crystals precipitated are collected by filtration and further recrystallized from methanol-isopropyl ether to give 14 g of 4-oxo-4-[4-(4-(4-(3-methylphenyl)piperazin-1-yl)butyl)phenyl]butyric acid having a melting point of 199° to 201° C.

The following compounds are obtained in the same manner as in Reference Example 1.

- ⊚ 4-Oxo-4-[4-(4-(4-(3-trifluoromethylphenyl)piperazin-1-yl)butyl)phenyl]butyric acid, melting point 120° to 122° C.
- ⊚ 4-Oxo-4-[4-(4-(4-(4-methylphenyl)piperazin-1-yl)butyl)phenyl]butyric acid, melting point 204° to 207° C.
- ⊚ 4-Oxo-4-[4-(4-(4-(2-methoxyphenyl)piperazin-1-yl)butyl)phenyl]butyric acid, melting point 162° to 165° C. with decomposition.
- ⊚ 4-Oxo-4-[4-(4-(4-(2-methylphenyl)piperazin-1-yl)butyl)phenyl]butyric acid, melting point 145° to 147° C.
- ⊚ 4-Oxo-4-[4-(4-(4-(4-methoxyphenyl)piperazin-1-yl)butyl)phenyl]butyric acid, melting point 185° to 187° C.
- ⊚ 4-Oxo-4-[4-(4-(4-(3-chlorophenyl)piperazin-1-yl)butyl)phenyl]butyric acid, melting point 168° to 169° C.
- ⊚ 4-Oxo-4-[4-(3-(4-phenylpiperazin-1-yl)propyl)phenyl]-butyric acid, melting point 175° to 178° C.
- ⊚ 4-Oxo-4-[4-(3-(4-(3-trifluoromethylphenyl)piperazin-1-yl)propyl)phenyl]butyric acid, melting point 164° to 167° C.
- ⊚ 4-Oxo-4-[4-(3-(4-(4-methylphenyl)piperazin-1-yl)propyl)phenyl]butyric acid, melting point 170° C.
- ⊚ 4-Oxo-4-[4-(2-(4-(3-methylphenyl)piperazin-1-yl)ethyl)phenyl]butyric acid, melting point 220° to 223° C. with decomposition.
- ⊚ 4-Oxo-4-[4-(2-(4-(2-pyrimidinyl)piperazin-1-yl)ethyl)phenyl]butyric acid, melting point 210° C. with decomposition.
- ⊚ 4-Oxo-4-[4-(4-(4-(2-pyrimidinyl)piperazin-1-yl)butyl)phenyl]butyric acid hydrochloride, melting point 207° to 210° C. with decomposition.

- 4-Oxo-4-[4-(4-(4-phenylpiperazin-1-yl)butyl)-phenyl]butyric acid hydrochloride, melting point 205° C. with decomposition.
- 4-Oxo-4-[4-(2-(4-(2-methoxyphenyl)piperazin-1-yl)ethyl)phenyl]butyric acid hydrochloride, melting point 245° to 248° C.

REFERENCE EXAMPLE 2

To 14 g of 4-oxo-4-[4-(4-(4-(3-methylphenyl)piperazin-1-yl)butyl)phenyl]butyric acid, 200 ml of ethanol is added. To this mixture, 3.1 g of hydroxylamine hydrochloride and 4.0 g of sodium hydrogencarbonate are further added, and this is followed by reflux with heating for 6 hours under stirring the mixture. After the completion of the reaction, the solvent is distilled off under reduced pressure. To this residue, water is added, and the crystals precipitated are collected by filtration to give 9.7 g of 4-hydroxyimino-4-[4-(4-(4-(3-methylphenyl)piperazin-1-yl)butyl)phenyl ]butyric acid having a melting point of 175° to 177° C.

The following compounds are obtained in the same manner as in Reference Example 2.

- 4-Hydroxyimino-4[4-(4-(4-(3-trifluoromethylphenyl) piperazin-1-yl)butyl)phenyl]butyric acid, melting point 178° to 180° C. with decomposition.
- 4-Hydroxyimino-4-[4-(4-(4-phenylpiperazin-1-yl)butyl)phenyl]butyric acid, melting point 196° to 197° C.
- 4-Hydroxyimino-4-[4-(4-(4-(2,3-dimethylphenyl)-piperazin-1-yl)butyl)phenyl]butyric acid, melting point 161° to 163° C. with decomposition.
- 4-Hydroxyimino-4-[4-(4-(4-(4-methylphenyl)piperazin-1-yl)butyl)phenyl]butyric acid, melting point 202° to 205° C. with decomposition.
- 4-Hydroxyimino-4-[4-(4-(4-(4-fluorophenyl)piperazin-1-yl)butyl)phenyl]butyric acid, melting point 185° to 187° C.
- 4-Hydroxyimino-4-[4-(4-(4-(2-methylphenyl)piperazin-1-yl)butyl)phenyl]butyric acid, melting point 174° to 176° C. with decomposition.
- 4-Hydroxyimino-4-[4-(4-(4-(4-methoxyphenyl)piperazin-1yl)butyl)phenyl]butyric acid, melting point 205° to 207° C.
- 4-Hydroxyimino-4-[4-(4-(4-(2-pyrimidinyl)piperazin-1-yl)butyl)phenyl]butyric acid, melting point 163° to 165° C.
- 4-Hydroxyimino-4-[4-(3-(4-phenylpiperazin-1-yl)propyl)phenyl]butyric acid, melting point 195° to 198° C. with decomposition.
- 4-Hydroxyimino-4-{4-(3-(4-(3-trifluoromethylphenyl)piperazin-1-yl)propyl)phenyl]butyric acid, melting point 129° to 131° C.
- 4-Hydroxyimino-4-[4-(3-(4-(4-methylphenyl)piperazin-1-yl)propyl)phenyl]butyric acid, melting point 177° to 179° C.
- 4-Hydroxyimino-4-[4-(2-(4-(3-trifluoromethylphenyl)piperazin-1-yl)ethyl)phenyl]butyric acid, melting point 189° C. with decomposition.
- 4-Hydroxyimino-4-[4-(2-(4-(4-methoxyphenyl)piperazin-1-yl)ethyl)phenyl]butyric acid, melting point 227° to 229° C. with decomposition.

INDUSTRIAL APPLICABILITY

The compounds of the present invention possess antipsychotic activities with less adverse reaction on the extrapyramidal system and are useful as antipsychotic drugs.

The present invention has been described in detail in the specification, particularly in the Disclosure of the Invention; however, this invention may be subjected to various alterations and modifications, without departing from the spirit or scope thereof.

What is claimed is:

1. A piperazine compound represented by the formula:

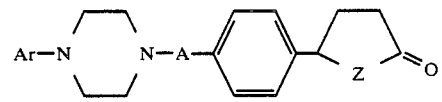

wherein Ar represents phenyl or phenyl having a substituent selected from the group consisting of halogen, lower alkyl and trifluoromethyl; A represent lower alkylene; and Z represents —NR— wherein R represents a hydrogen atom, or a pharmaceutically acceptable acid addition salt thereof.

2. The piperazine compound as claimed in claim 1, which is selected from the group consisting of 5-[4-(4-(4-(3-trifluoromethylphenyl)piperazin-1-yl)butyl)-phenyl]pyrrolidin-2-one, 5-[4-(2-(4-(3-trifluoromethylphenyl)piperazin-1-yl)ethyl)phenyl]pyrrolidin-2-one, 5-[4-(4-(4-(3-methylphenyl)piperazin-1-yl)butyl)-phenyl]pyrrolidin-2-one, 5-[4-(3-(4-phenylpiperazin-1-yl)propyl)phenyl]pyrrolidin-2-one, 5-[4-(4-(4-(4-fluorophenyl)piperazin-1-yl)butyl)phenyl]pyrrolidin-2-one, and a pharmaceutically acceptable acid addition salt thereof.

3. A pharmaceutical composition for the treatment of schizophrenia or mania which comprises a piperazine compound as claimed in claim 1 or a pharmaceutically acceptable acid addition salt thereof as active ingredient, and a pharmaceutically acceptable carrier, excipient, diluent or solubilizer therefor.

* * * * *